US00PP14009P29

(12) United States Plant Patent
Bourne

(10) Patent No.: US PP14,009 P2
(45) Date of Patent: Jul. 22, 2003

(54) GRAPEVINE PLANT NAMED '14-37-111'

(75) Inventor: Timothy F. Bourne, Visalia, CA (US)

(73) Assignee: SunView Vineyards of California, Inc., Delano, CA (US)

( * ) Notice: Subject to any disclaimer, the term of this patent is extended or adjusted under 35 U.S.C. 154(b) by 0 days.

(21) Appl. No.: 10/073,940

(22) Filed: Feb. 14, 2002

(51) Int. Cl.[7] ..... A01H 5/00
(52) U.S. Cl. ..... Plt./205
(58) Field of Search ..... Plt./205

*Primary Examiner*—Bruce R. Campell
*Assistant Examiner*—Susan B. McCormick
(74) *Attorney, Agent, or Firm*—Jondle & Associates PC

(57) ABSTRACT

This new variety '14-37-111' is new and different because of its unusual shape, early ripening, very firm texture and very large berry size. It differs from other early ripening red grapes such as 'Flame Seedless' (not patented) in having an ovate berry shape and much larger berry. It differs from other later ripening red, seedless grapes such as 'Crimson Seedless' (not patented) due to its greater fruitfulness and much larger berry size following applications of exogenous gibberellic acid and trunk girdling.

3 Drawing Sheets

Genus and species: *Vitis vinifera.*

BACKGROUND AND SUMMARY OF THE INVENTION

The new table grapevine '14-37-111' is of *Vitis vinifera* parentage and resulted from a twenty year breeding program which had as its goal the development of an early-ripening, brightly colored, red, seedless table grape. The female, seed parent was an unnamed and unpatented plant resulting from a series of crosses involving 'Hunisa', 'Flame Seedless', 'Emperor', and 'Thompson Seedless'. The male parent of the cross is an unnamed and unpatented, seedless grapevine resulting from a series of crosses involving 'Emperor', 'Thompson Seedless', 'Muscat of Alexandria', and 'Calmeria'. The hybridization resulting in '14-37-111' was made in 1993 near McFarland, Calif. The seedling was selected from a population of 47 seedlings of like parentage in 1996. It was then propagated by cuttings and grafting to variety 'Freedom' rootstock. This new variety has been found to retain its distinctive characteristics through successive propagations; and this novelty is firmly fixed.

The new grapevine variety, cultivar '14-37-111' is similar to the seeded cultivar 'Emperor', from which it descends, but differs from it by being seedless, with traces that are not noticeable due to their small size and the crisp flesh of the berry. '14-37-111's ripening period is much earlier in the year, ripening approximately 1 week later than cultivar 'Flame Seedless' (unpatented) at Delano, Calif. The present variety differs from 'Flame Seedless' by having an ovate berry shape and a having a much brighter red berry color and ripening about one week later than 'Flame Seedless'. It differs from the cultivar 'Crimson Seedless' by having a much greater fruitfulness, yielding one or two clusters from spur-pruned vines, being less vigorous in its growth habit, and ripening about three weeks earlier at Delano, Calif.

DESCRIPTION OF THE FIGURES

The accompanying drawings illustrate the following.

DETAILED BOTANICAL DESCRIPTION OF THE INVENTION

Figure 1:
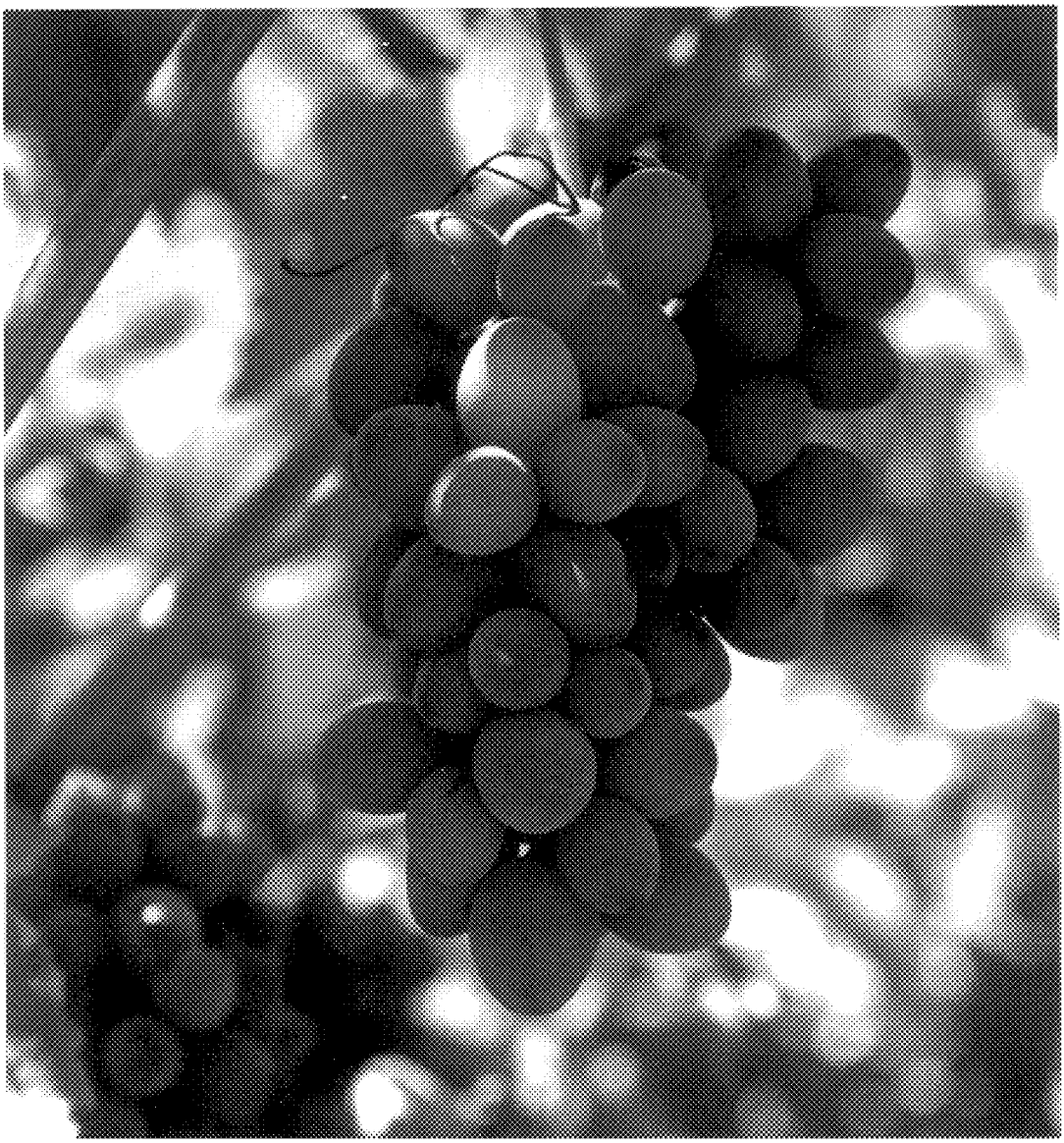
FIG. 1 illustrates the fruit cluster at harvest.
Figure 2:
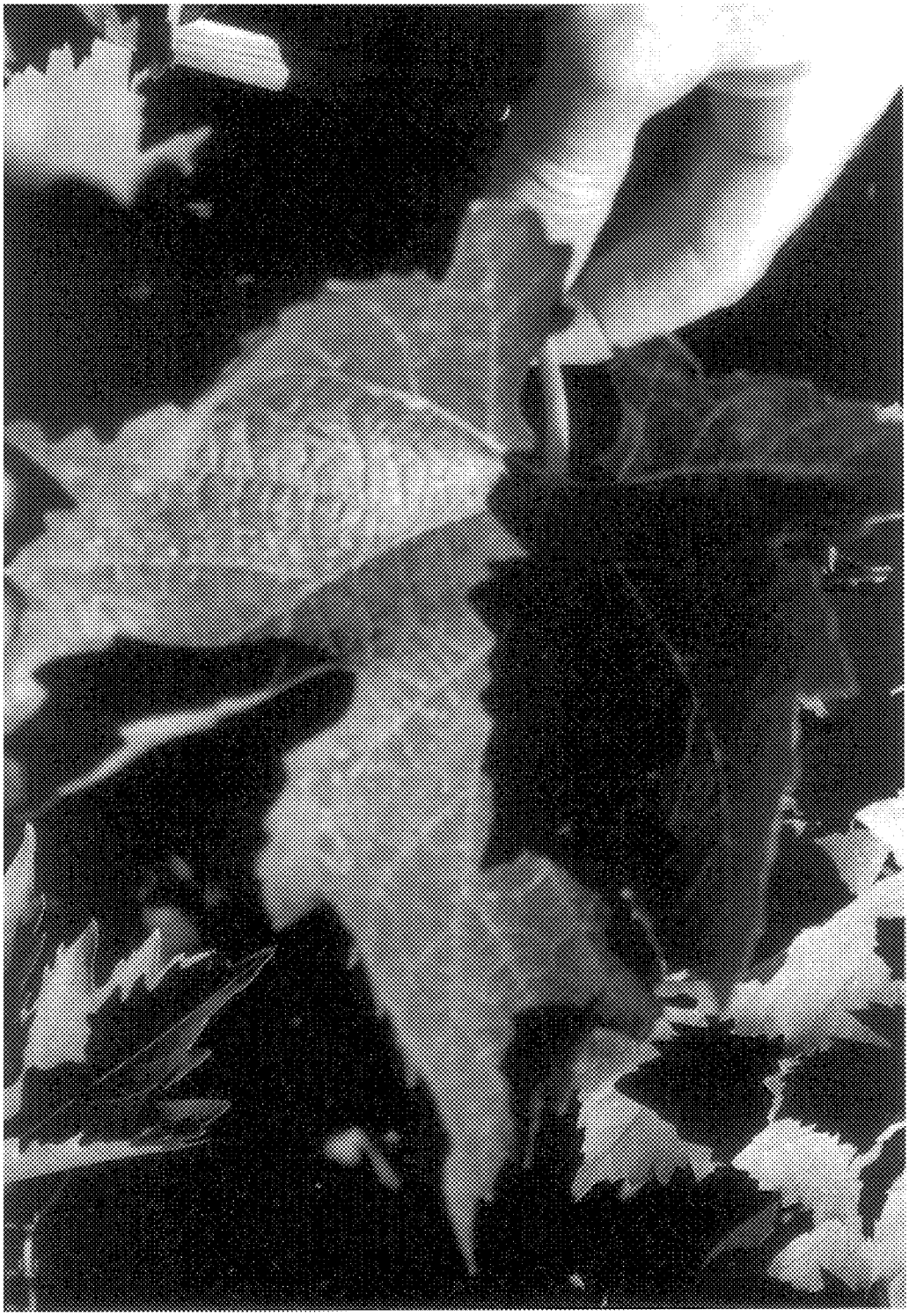
FIG. 2 illustrates the mature leaf.
Figure 3:
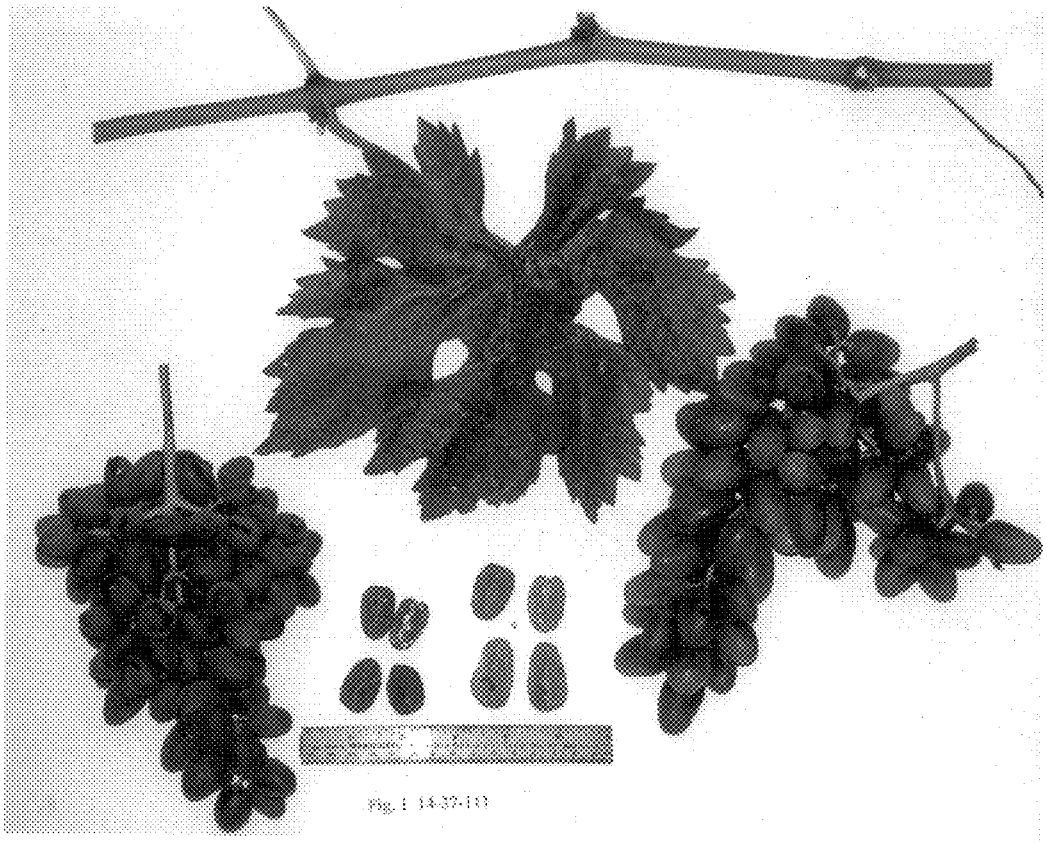
FIG. 3 shows the cane, leaf, natural fruit cluster (left) and fruit cluster following gibberellic acid applications (right).

The following description of grapevine '14-37-111' contains references to color names taken from The Munsell Color Chart for Plant Tissues, published by Munsell Color, New Windsor, New York. Descriptors used herein conform to those set forth by the International Board for Plant Genetic Resources Institute Grape Descriptors (Vitis spp.) of 1983 and/or 1997 which were developed in collaboration with the Office Interantional de la Vigne et du Sin (OIV) and the International Union for the Protection of New Varieties of Plants (UPOV).

Descriptions of the new invention apply to vines of '4-37-111' grown on 'Freedom' rootstock at a density of 1,537 vines per hectare grown in Kern County, Calif. in 2001. These vines were in their first year of full production having been planted in 1998. These descriptions are believed to apply generally to the new variety grown under similar circumstances elsewhere:

VINE

General:

*Size.*—3 year old vines on 'Freedom' rootstock are average size — trunk diameter is 100 cm; height is 34 mm.

*Vigor.*—3 year old vines on 'Freedom' rootstock are average vigor — cane length on vines thinned to 32 shoots averaged 2.15 meters of growth from March–September, 2001.

*Density of foliage.*—Moderate.

*Productivity.*—Very productive when spur pruned, up to 49,000 kg./hectare.

*Trunk circumference.*—16.4 cm. at 1 meter height.

*Rootstock.*—Freedom.

Trunk:

*Shape.*—Circular.

*Straps.*—Long, split.

*Surface texture.*—Shaggy.

*Inner bark color.*—2.5YR 5/6.

LEAVES

Mature leaves:
*Average blade length.*—16.0 cm.
*Average blade width.*—20.9 cm.
*Size of blade.*—Medium to large.
*Shape.*—Pentagonal.
*Anthocyanin on main veins on the upper side of the blade.*—Absent.
*Mature leaf profile.*—Flat.
*Blistering surface of blade upper surface.*—Absent.
*Leaf blade tip.*—In plane of the leaf.
*Undulation of margin.*—Slight.
*Apex.*—Narrowly acuminate.
*Thickness.*—Medium.
*Undulation of blade between main and lateral veins.*—Slight.
*Shape of teeth.*—Conical, both sides convex.
*Length of teeth.*—5–15 mm.
*Ratio length/width of teeth.*—About 1:1.
*General shape of petiole sinus.*—Variable — open (ovate) to closed.
*Tooth at petiole sinus.*—Absent.
*Petiole sinus limited by veins.*—Absent.
*Shape of upper lateral sinus.*—Shallow with lobes overlapping strongly.
*Prostrate hairs between veins on lower surface of blade.*—Absent.
*Erect hairs between hairs on lower surface of blade.*—Absent.
*Prostrate hairs on main veins on lower surface of blade.*—Absent.
*Density of erect hairs on main veins on lower surface of blade.*—Medium — hairs distributed along entire length of main veins.
*Prostrate hairs on main veins on upper surface of blade.*—Absent.
*Autumn coloration.*—2.5Y 7/8 to 5Y 8/6.

Upper surface:
*Color.*—7.5 GY 4/4 to 4/6.
*Surface texture.*—Smooth.
*Surface appearance.*—Dull.
*Goffering of blade.*—Absent.

Lower surface:
*Color.*—5GY 5/6 to 5/10.
*Anthocyanin coloration of main veins on lower leaf surface.*—Absent.
*Glossiness.*—Low.
*Pubescence.*—Absent.
*Surface texture.*—Smooth.
*Surface appearance.*—Dull.

Petiole:
*Length of petiole.*—11.0 cm.
*Diameter of petiole at* 4 cm from base.—2 mm.
*Length of petiole compared to middle vein.*—Considerably shorter.
*Color of petiole.*—2.5GY 8/10.
*Density of prostrate hairs on petiole.*—Absent.
*Density of erect hairs on petiole.*—Absent.
*Shape of base of petiole sinus.*—Mostly closed, inside outline is ovate.

Woody shoot:
*Shape.*—Stocky.
*Internode length.*—About 13.0 cm.
*Width at node.*—About 1.5 cm.
*Cross section.*—Circular.
*Surface.*—Smooth.
*Main color.*—5YR 5/8 to 5/10.
*Lenticels.*—Inconspicuous.
*Erect hairs on nodes.*—Absent.
*Erect hairs on internodes.*—Absent.
*Growth of axillary shoots.*—Prolific.

Buds:
*Shape.*—Conical.
*Cane bud fruitfulness.*—Basal buds fruitful, 1–2 clusters per shoot.

FLOWERS

General:
*Flower sex.*—Perfect.
*Length of first inflorescence.*—21.2 cm.
*Position of first flowering nodes.*—$3^{rd}$ to $4^{th}$.
*Number of inflorescences per shoot.*—1 or 2.
*Date of full bloom.*—May 9, 2001.
*Time of bloom.*—Early compared to other varieties growing in the area around McFarland, Calif.

FRUIT

General:
*Ripening period.*—Early; about 1 week after 'Flame Seedless' at Delano, Calif.
*Date of ripening.*—About July 13.
*Use.*—Fresh market.
*Keeping quality.*—Very good.
*Disease.*— *No disease symptoms have been observed on vines in* 3 years of growth.
*Insect.*—Grape leafhopper, *Erythroneua elegantula* (Osborn) and variegated leafhoppers, *Erythroneura variabilis* (Beamer) have been observed feeding on vines. No other predaceous insects have been observed.
*Shipping quality.*—Good.
*Date of first harvest.*—Jul. 20, 2001.
*Solids-sugar.*—High, about 25 brix at full maturity.
*Refractometer test.*—26.0 brix.

Cluster:
*Bunch size.*—Medium.
*Bunch length* (*peduncle excluded*).—About 22 cm.
*Bunch width.*—About 12 cm.
*Bunch weight* (*natural*).—359 g.
*Bunch weight* (*gibberellic acid treated*).—1,069 g.
*Bunch density.*—Very dense.
*Number of berries.*—127.
*Form.*—Conical.

Peduncle:
*Length of peduncle.*—4 cm.
*Lignification of peduncle.*—Strong, upper 2 cm.
*Color.*—5YR 5/4.

Berry:
*Size.*—Medium.
*Uniformity of size.*—Uniform.
*Berry weight* (*natural*).—4.8 g.
*Berry weight* (*gibberellic acid treated*).—7.2 g.
*Shape.*—Ovate.
*Presence of seeds.*—Rudimentary.
*Cross section.*—Circular.
*Dimensions.*—Longitudinal axis~2.3 cm.; horizontal axis~1.7 cm.
*Skin color* (*without bloom*).—5R 4/8 to 4/10.
*Coloration of flesh.*—Clear.
*Juiciness of flesh.*—Very juicy.

*Berry firmness.*—Very firm.
*Particular flavor.*—Neutral, typical vinifera.
*Bloom* (*cuticular wax*).—Strong.
*Pedicel length.*—5 mm.
*Berry separation from pedicel.*—Moderate.

Skin:
*Thickness.*—Medium.
*Texture.*—Smooth.
*Reticulation.*—Absent.
*Tenacity.*—Tenacious to flesh.
*Tendency to crack.*—Resistant.

Tendrils: Bifurcated or trifurcated, 15.5 cm from base to tip of longest branch.

What is claimed is:

1. A new and distinct variety of grapevine plant, substantially as illustrated and described.

* * * * *